Figure 1:
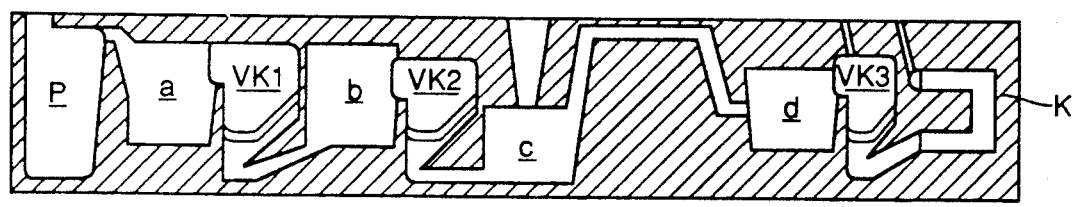

United States Patent [19]
Mangold et al.

[11] Patent Number: 5,177,022
[45] Date of Patent: Jan. 5, 1993

[54] IMMUNE REACTIVE POROUS CARRIER MATERIAL

[75] Inventors: Dieter Mangold, Maxdorf; Siegfried Noetzel, Wilhelmsfeld; Rolf Lerch, Ilvesheim; Jelmut Jering, Tutzing, all of Fed. Rep. of Germany

[73] Assignee: Boehringer Mannheim GmbH, Mannheim, Fed. Rep. of Germany

[21] Appl. No.: 236,458

[22] Filed: Aug. 25, 1988

[30] Foreign Application Priority Data

Oct. 22, 1987 [DE] Fed. Rep. of Germany ....... 3735684

[51] Int. Cl.⁵ ............... G01N 33/551; G01N 33/544; G01N 33/549
[52] U.S. Cl. ................... 436/524; 436/531; 436/532
[58] Field of Search ............... 424/78, 85.8; 436/531, 436/524, 532

[56] References Cited

U.S. PATENT DOCUMENTS

| | | | |
|---|---|---|---|
| 3,888,629 | 6/1975 | Bagshawe | 436/542 |
| 4,504,582 | 3/1985 | Swann | 424/78 |
| 4,786,606 | 11/1988 | Giegel et al. | 436/500 |
| 4,803,171 | 2/1989 | Baier et al. | 436/531 |
| 4,820,633 | 4/1989 | Herrmann | 436/531 |
| 4,820,644 | 4/1989 | Schafer et al. | 436/826 |

Primary Examiner—Lester L. Lee
Assistant Examiner—Pili Curtis
Attorney, Agent, or Firm—Felfe & Lynch

[57] ABSTRACT

The present invention provides an immune reactive porous carrier material comprising a porous carrier material with immune complexes precipitated thereon, wherein the porous carrier material is treated with at least one wet-strength agent.

The present invention also provides processes for the production of this immune reactive porous carrier material.

11 Claims, 1 Drawing Sheet

IMMUNE REACTIVE POROUS CARRIER MATERIAL

The present invention is concerned with an immune-reactive porous carrier material and a process for the production thereof.

Immune-reactive porous carrier materials play an important part in various branches of technology. For example, such materials are needed for analytical and preparative processes in which a component of an immune reaction is used which is fixed to an insoluble carrier. The fixing of the component of the immune reaction to the insoluble carrier can take place by chemical or physical forces.

Thus, methods have been known for a long time for the production of covalent bonds between a solid carrier material and a chemical substance to be bound thereon, including especially biologically active substances. In general, a disadvantage of these methods is that they bring about a chemical change of the biologically active material which, in many cases, can also result in changes in the biological activity of the substance thus bound.

Another known method is the inclusion polymerisation of such biologically active substances. As a rule, the molecule here remains unchanged and, therefore, also its biological activity is also unchanged. However, the accessability for the other component of the immune reaction present in a liquid phase is drastically limited.

Therefore, in many cases, the third known process was used which avoids the disadvantages of covalent binding and of inclusion polymerisation, namely, the adsorptive fixing of soluble substances onto an appropriate carrier material. However, this method in turn also has the disadvantage that the bonding to the solid carrier is substantially weaker than in the case of the first two mentioned methods.

Special problems arise with regard to the strength of adsorptive binding when porous carrier material are used. From U.S. Pat. No. 3,888,629 a method is known which reduces this problem by carrying out the fixing in the pores of the carrier material by allowing a precipitation reaction to take place between the two components of an immune reaction, i.e. between antibody and antigen or hapten. In this method, the two solutions of the components of the immune reaction in question are rapidly mixed and then the porous material immediately impregnated therewith. A variant of this method is described in WO 82/02601 in which the porous carrier material is impregnated with a solution of the first component of the immune reaction and thereafter treated with a solution of the second component of the immune reaction so that the immune reaction itself can take place in the porous carrier material, with permanent fixing of the desired immune reactive material without chemical change or disadvantages with regard to its accessibility for other reaction components.

This method of binding an immune reactive material to a porous carrier material admittedly reduces the above-described problems but, nevertheless, displays other problems, namely, non-uniform distribution of the fixed immune reactive substance on the carrier material. This disadvantage is especially serious when this immune reactive porous carrier material is to be used, for example, for the quantitative analysis of haptens or proteins of low concentration. The requirement of stability of the antigen-antibody precipitate, as well as of low equilibrium-dissociation concentrations of the immune reactive component of the immune complexes relative to the concentration of the hapten or protein to be determined, can only be achieved when the antibody used has a high affinity for the particular antigen. As is known to those skilled in the art, the precipitation formation takes place spontaneously upon mixing such immune reactive components. In the production of large amounts of immune reactive porous carrier materials using the impregnation method described supra expected uncontrollable precipitation occurs over time and the carrier.

Quantitative measuring of immunosorbent is generally carried out by, e.g. cutting out a defined area of immune reactive paper, by using a defined number of spheroidal porous carrier material, or by weighing out a definite amount of the immune reactive carrier material. When using fixed immune reactive material where the immune reactive material is not uniformly distributed as described supra, these simple requirement methods cannot be used.

A further disadvantage of the known immune precipitation technique is that it requires very highly purified antigen, which makes necessary a pre-purification by immunosorption and thus an expensive method of production.

A uniform distribution of the immune complex precipitate in the carrier material is achieved by the "homogeneous" process which is described in Federal Republic of Germany Patent Specification No. 34 46 636. According to this method, a porous carrier material is impregnated with a solution of both components of the immune reaction which is mixed with an inhibiting material for the prevention of precipitation. By removal of the inhibiting material, for example by drying an impregnated fleece, the precipitation is initiated. If the immune components have not been mixed together in the ratio of the Heidelberger maximum at which the resulting turbidity is maximum, the excess of one of the immune components must be rinsed off by washing the carrier material. Immune complexes which are not firmly adsorbed, as well as easily dissociating immune complexes, are thereby washed from the carrier material. If the immune components are used at the Heidelberger maximum for the precipitation, then an additional washing step for the removal of an excess of one of the reaction components is admittedly no longer necessary. However, immune complexes which are not firmly bound or which dissociate easily remain on the porous carrier material and can cause disturbances. If, for example, an immune reactive carrier material produced in the above-described manner is used for the quantitative determination of an immune reactive analyte, then the concentration value measured for the analyte is falsified since, by washing out components relevant for the measurement or for a measurement reaction, a blank value results for the measurement in the measurement medium. Depending upon the measurement method, this then leads to too high or too low a value for the analyte concentration to be determined.

It is an object of the present invention to provide an immune reactive porous carrier material in which these disadvantages are avoided and especially in which the immune complexes adhere more firmly to the carrier material.

Thus, according to the present invention, there is provided an immune reactive porous carrier material comprising a porous carrier material with immune complexes precipitated thereon, wherein the porous carrier material is treated with at least one wet-strength agent.

The present invention also provides a process for the production of an immune reactive porous carrier material by precipitating an immune complex on a porous carrier material, wherein the porous carrier material is treated with at least one wet-strength agent and the immune complexes are subsequently precipitated thereon.

The wet-strength agent(s) can, if desired, already be added to the fibre pulp, the porous carrier material is subsequently dried and the immune complexes are precipitated thereon.

An important feature of the process aspect of the invention described herein is the use of materials which, at the end point of the working up, are either insoluble or only slightly soluble in water and which surround the fibres of the original carrier material. Such materials are, in particular, the wet-strength agents sometimes used in the making of paper. They provide for a better mechanical loading capacity of the paper. The wet strength, which in general is lowered in comparison with the dry strength, is increased (see Zellstoff, Papier, 5th edition 1979, pub. VEB Fachbuchverlag Leipzig, pp. 233-235). Naturally, in general, the dry strength is also increased in comparison with untreated papers.

It was surprising that the use of wet-strength agents brings about considerable advantages for immune reactive porous carrier materials produced using these.

In producing carrier materials treated with wet-strength agents, the general methods and apparatus used in producing paper can be used in the absence of any statement to the contrary.

According to the present invention, as fibrous starting materials for the production of carrier materials treated with wet-strength agents, there can be used mixtures of cellulose fibres of various origin and properties, preferably sulphite wood pulp, regenerated cellulose, viscose fibres and linters, with fibres of synthetic polymers and preferably of generally conventional polyesters, polyamides and polyacrylonitriles. The amount of these synthetic resin fibres in the total mass is limited by their working up ability. With generally conventional paper machines, there can be produced, for example, carrier materials with up to 95% and preferably up to 60% by weight of synthetic resin fibre material, the remainder being made up of cellulose fibres of the above-mentioned kinds.

The length of the fibres is of no great importance for the present invention. However, it has proved to be advantageous to use fibres with a length of from 1 to 6 mm.

From the fibres, there is prepared a fibre pulp in the manner conventional in the production of paper, which pulp contains the fibres in the desired length, possibly after commination.

At least one wet-strength agent is now added to this fibre pulp. Conventional wet-strength agents include epichlorohydrin resin, melamine-formaldehyde resin, urea-formaldehyde resin, polyethyleneimine and especially carboxymethylcellulose and mixtures thereof. These can be used in the process according to the present invention. For use within the meaning of the present invention, there can also be used materials of the above-mentioned classes of substances which admittedly do not themselves possess any outstanding wet-strength properties but, nevertheless, have the same effect in the meaning on reagent carriers as do the wet-strength agents as described therein.

The commercial products Luresin ®, Tylose ®, Madurit ®, Etadurin ® and Urecoll ® have proved to be especially preferred. Luresin is a polyamidoamine-epichlorohydrin resin, Tylose is a carboxy-methyl-cellulose, Madurit is a melamine-formaldehyde resin, Etadurin is a polyamidoamine-epichlorohydrin resin and Urecoll (BASF AG) is a urea-formaldehyde resin. According to the present invention, there can also be used a mixture of wet-strength agents of the above-mentioned types or equivalent compounds.

The proportion of wet-strength agents in the fibre pulp depends upon the particular wet-strength agent used but is advantageously from 0.05 to 6% by weight and preferably 2 to 4% by weight, referred to the amount of cellulose fibre material used. Naturally, more of the wet-strength agent can also be added but this does not lead to a marked improvement in the meaning of the present invention.

If desired, other adjuvant materials can also be introduced into the fibre pulp, for example, hardeners, binders, strengtheners, pigment materials or size.

The porous carrier material is produced in the usual way from the fibre pulp on a paper machine, the flow-off rate of the liquid thereby influencing the density of the resulting porous carrier material. The density of the carrier material can be further increased by subsequent pressing.

In the following drying procedure, which can be carried out at an elevated temperature, the porous carrier materials treated with wet-strength agents can possibly also be aged. Thus, for example, in the case of melamine-formaldehyde resins, which are used as water-soluble pre-condensates, this includes the continuation or ending of the condensation.

The porous carrier materials treated with wet-strength agents produced according to the above-described process are to have a density of 0.2 to 0.5 g./cm$^3$ and preferably of 0.3 to 0.4 g./cm$^3$. Otherwise, the dried porous carrier materials treated with wet-strength agents are calendered. All carrier materials which have such a density have hollow spaces between the fibres from which they are built up and thus are porous.

The production of a carrier material treated with wet-strength agents can, however, also take place in another way. According to a further preferred embodiment, the wet-strength agent is not added to the fibre pulp but rather the carrier material produced on a paper machine without the addition thereof is impregnated in an impregnation machine with a solution of the wet-strength agent. The concentration of the wet-strength agent in the solution is thereby from 0.01 to 0.6% by weight and preferably from 0.35 to 0.45% by weight. Subsequently, the porous carrier material treated with the wet-strength agent is dried at a temperature of from 50° to 150° C. and preferably of from 80° to 100° C. to a residual moisture content of 2 to 6% by weight and preferably of about 3% by weight.

The expert is aware of further appropriate possibilities of producing carrier materials treated with wet-strength agents, for example dry deposited fleece.

The carrier materials treated with wet-strength agents preferably have a wet-strength agent content of about 0.05 to 6% by weight and more preferably of from 2 to 4% by weight, referred to the amount of cellulose fibre material used.

The immune complexes are now adsorbed on to the so produced porous carrier materials treated with wet-strength agents, immune reactive porous carrier materials thereby being obtained.

By immune reactive carrier materials are to be understood carrier materials which can act as immune components in an immunological reaction via the immune complexes precipitated thereon. This can take place via the following partial structures of the immune complexes:

via further immune reactive antigenic determinants of the antibody and/or antigen part of the immune complexes, via further free antigen-binding sites of an antibody of the immune complexes; these antibodies can thereby be bound in the precipitated immune complex as antibody or as antigen part, via groups which display a specific, non-immunological binding exchange action to another substance; these include, for example, strong enzyme-substrate, enzyme-coenzyme and enzyme-inhibitor interactions.

The components of the immune precipitation in the scope of the process according to the present invention are, on the one hand, an antigen, for example a hapten or a protein, and, on the other hand, an antibody. The antigen can naturally itself also be an antibody. The antibodies can hereby be not only monoclonal but also polyclonal. By antibodies are to be understood not only the complete antibodies but also fragments thereof, for example Fab, Fab' and (Fab')$_2$ fragments.

When a precipitating anti-antibody is used for the precipitation, it must be appropriately selected. The anti-antibody itself can then be polyclonal or monoclonal or a (Fab')$_2$ fragment thereof. Mixtures of monoclonal antibodies can also be used as anti-antibody fraction for the immune precipitation.

As immune reactive material to be precipitated, there can preferably also be used a protein to which a hapten or antigen is coupled. In this case, a precipitating antibody is advantageously used as second component of the immune reaction which is directed against the protein. In a further embodiment, a hapten or antigen can be coupled to the precipitating antibody. The other component of the immune reaction can thereby be unlabelled or coupled with the same or another hapten or antibody. Alternatively, the protein to be precipitated is itself a specific antibody which is precipitated by an anti-antibody. Furthermore, a hapten or antigen can be coupled to the antibody to be precipitated. The precipitating antibody can then be directed not only against the antibody but also against a part of the antibody or against the hapten or antigen bound thereon.

The terms antibody, antigen and hapten also include substances which, besides the binding sites for the precipitating component or component to be precipitated of the immune reaction, have at least one further binding site for a component of a further immune reaction or of another reaction, in the case of which specific interactions, for example enzyme-substrate, enzyme-coenzyme or enzyme-inhibitor interactions, are utilised.

There are several possibilities for the precipitation of the immune component on the carrier material. There is a differentiation between heterogenous processes, such as are described, for example, in WO 82/02601 and in U.S. Pat. No. 3,888,629, and homogenous processes. Not only heterogenous but also homogenous precipitation processes can be used in the process according to the present invention. Especially preferred are the homogenous 1-step and the homogenous 2-step processes described in Federal Republic of Germany Patent Specification No. 34 46 636. In the first process, the carrier material treated with wet-strength agent is impregnated with a solution which contains the immune components in the ratio of the Heidelberger maximum and at least one appropriate inhibitor. Thereafter, it is dried to a definite residual moisture content, for example of 3% of weight.

In the second process, the carrier material treated with the wet-strength agent is first impregnated with a solution of a material removing the inhibition, for example sodium chloride, then dried and subsequently impregnated with a solution which contains the immune components in the ratio of the Heidelberger maximum and at least one appropriate inhibitor for the precipitation. The precipitation and the adsorption on the surface of the carrier material treated with the wet-strength agent take place during the subsequent drying.

A great advantage of the process according to the present invention for the production of immune reactive porous carrier materials is that washing steps, which are laborious and, furthermore, produce micro- and macro-inhomogeneities in the covering of the surface of immune reactive porous carrier materials by the immune complexes, can be omitted. There is thereby produced a very homogenous, immune reactive porous carrier material.

Furthermore, immune reactive porous carrier materials are made available by the process according to the present invention on which the immune complexes are firmly adsorbed and do not bleed out during the carrying out of immunological tests. Thus, the blank values of the measurements involved therewith can be avoided which means a simplification of the carrying out of the test.

However, the immune reactive carrier materials produced according to the present invention can also be used for tests and separation processes in which one or more washing steps cannot be avoided for reasons caused by the process. Since the immune complexes adhere very firmly to the surface of the carrier material, the concurrent washing out and thus loss of the immune complexes before or during the test or the separation process is reduced. The result of this is that it is possible to use less immune complexes for the test or the separation process and the immune capacity of the immune reactive carrier material remains the same.

The ability to produce, according to the present invention, a very homogenous immune reactive porous carrier material enables it to be used independently of its shape and size. The carrier materials treated with wet-strength agents can be shaped not only as described in paper-like form but also, for example, in other geometrical forms, for example in the form of columns or blocks.

For the production of carrier materials treated with wet-strength agents with these other different geometric shapes, the wet-strength agent can also be added not only to the fibre pulp but the carrier material can also first be given any desired geometrical shape and subsequently impregnated with a solution of the wet-strength agent in the above-described manner and then dried.

Immune reactive porous carrier material produced according to the present invention can be used in a heterogenous immunoassay for the qualitative or quantitative determination of an analyte, for example of a hapten, antigen or antibody. For example, in such an assay, a hapten (Hp) or an antigen (Ag) or an antibody (Ab), which is contained in a sample, such as, a buffer solution, serum, plasma, urine, culture supernatant or the like, is mixed with a labelled binding component (B). For this purpose, there can be used, inter alia, antibodies and antibody fragments, as well as ligands, which react specifically with the hapten or antigen, or hapten or antigen. As labelling, there can be used, for example, an enzyme, a fluorescent label or a radioisotope. The amount of the added binding component can be in molar insufficiency with respect to the analyte, such as the hapten, antigen or antibody present in the sample. The amount used will vary, depending upon the particular test.

This mixture is incubated for a constant time, during which the complexes Hp-B, Ag-B or Ab-B are formed. After expiry of this period of time, three species are present in the reaction mixture, namely, the complex, consisting of hapten, antigen or antibody and binding components (Hp-B, Ag-B, Ab-B), free hapten or antigen or antibody (Hp, Ag, Ab) and free binding component (B).

The separation of these species takes place in a second step by means of immunosorption. For this purpose, the mixture is applied to the immune reactive porous carrier material produced according to the present invention on which, depending upon the chosen immunological measurement method, there is precipitated either the hapten or antigen to be detected or the antibody directed theragainst.

As immunological measurement process for the determination of haptens, there is especially preferred the so-called IEMA process: The immune reactive carrier material with precipitated hapten binds the free binding component which is, however, not saturated with hapten. Consequently, the supernatant or the eluate of the solid phase contains the binding component saturated with the hapten of the sample. The quantitative determination of the hapten now takes place via the labelling of the binding component.

For the determination of the antigen, there is preferred the so-called sandwich process: For this purpose, an immmune reactive carrier material is used on which is precipitated an antibody directed against the antigen to be determined. This binds the complex of antigen and binding component but not the free binding component. Residues of the free binding component are removed by washing. The quantitative detection of the antigen takes place via the labelling of the binding component.

Another use is in competitive immune tests: The use of the immune reactive carrier material produced according to the present invention can take place in such a manner that the sample, which contains the analytes (hapten, antigen or antibody), is mixed with a constant amount of labelled analyte. The labelling can be, for example, an enzyme, a fluorescent label, a radioisotope and some other type of label. This mixture is applied to the immune reactive carrier material. On this is precipitated an immunological component which is directed against the analyte. The mixture is incubated on the immune reactive carrier material for a definite period of time. During this time, not only unchanged analyte but also labelled analyte compete for the binding sites of the immunological component on the immune reactive carrier material. The more analyte is present in the sample, the less labelled analyte is bound by the immune reactive carrier material and vice versa. At the end of the incubation phase, the liquid is removed from the porous immune reactive carrier material, for example by centrifuging. There is then determined either the amount of labelled analyte in the free phase or the amount of labelled analyte bound to the solid phase.

A further use of the immune reactive carrier material produced according to the present invention can take place in such a manner that the analyte (hapten, antigen or antibody) is mixed with a known amount of labelled immunological component which is directed against the analyte. Possible types of labelling have been described hereinbefore. This mixture is either incubated for a definite period of time and then applied to the porous immune reactive carrier material or, alternatively, is applied to the porous immune reactive carrier material immediately after mixing. When the analyte is a hapten, the immune reactive carrier material contains the hapten to be detected or a derivative thereof, also in precipitated form. If the first mixture has been incubated before application to the carrier material, then still free labelled immunological component binds to the immune reactive porous carrier material. If the mixture is immediately applied to the immune reactive carrier material, then the analyte from the sample and the analyte fixed on the immune reactive carrier material compete for the binding sites of the labelled immunological component. At the end of the incubation phase, the sample liquid is separated from the immune reactive porous carrier material and the amount of labelled immunological component is determined either in the liquid phase or on the immune reactive porous carrier material.

The immune reactive porous carrier materials produced by the process according to the present invention can be used as matrix fleece in the case of immune tests. By way of example, there may be mentioned:

1. The use of insert elements according to European Patent Specification No. 0,167,171 or according to European Patent Specification No. 0,073,513 (for example FIG. 1);

2. The use in an immune test strip, the liquid in which the analyte is dissolved here being transported by capillary force from one fleece to the next.

Figure 2:
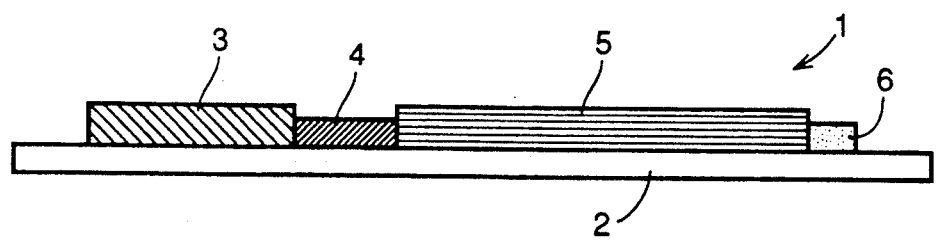

The construction of a simple test strip is illustrated in FIG. 2 of the accompanying drawings.

The test strip 1 consists of a carrier layer 2 and fleeces 3, 4, 5 and 6 fixed thereon. The liquid is applied to fleece 3 and dissolves the necessary reagents, for example a labelled antigen, hapten or antibody, from fleece 4. Fleece 5 is an immune reactive porous carrier material according to the present invention. Finally, in fleece 6 the spectroscopic measurement of the labelling takes place. In the case of appropriate choice of the labelling, there can, for example, also be visually assessed a colour change. Such immune test strips can also be used in the scope of the automatic carrying out of tests.

The following Examples are given for the purpose of illustrating the present invention:

EXAMPLE 1

Production of Carrier Material Treated with Wet-Strength Agents by the Addition of a Wet-Strength Agent to the Fibre Pulp a) The following starting materials are used:
1000 liters water
2.4 kg. polyester (1.7 dtex., cut length 6 mm., absolutely dry; Schwarzwälder Textil Werke)
0.6 kg. sulphite wood pulp (Type FW absolutely dry; Bayerische Zellstoff GmbH)

0.018 kg. Luresin ® (BASF AG, corresponds to 3% by weight, referred to sulphite wood pulp).

A commercially available oblique screening machine is used as paper machine. The fibre materials are brushed out, ground and foamed with water and wet-strength agent. The resultant fibre pulp is pumped on to an oblique screen. Whereas the liquid runs off, the fibres are held back on the screen surface and transported to a drier. Drying takes place at 125° C. until a moisture content of 1.4 to 2.4% by weight is achieved. The sucking off and transport rates are so chosen that a material is obtained with a density of 0.33 g./cm³ and a thickness of 0.6 mm.

b) Analogously to Example 1a), a carrier material is produced from the following starting materials:
1000 liters water
1 kg. sulphite wood pulp (Type FW absolutely dry; Bayerische Zellstoff GmbH)
0.5 kg. cellulose wool viscose (Type DAB7, absolutely dry; 1.7 dtex, cut length 6 mm.; Rohtex Textil GmbH)
1 kg. polyamide (absolutely dry, 2.2 dtex, cut length 4 mm.; Schwarzwälder Textil Werke)
1 kg. polyester (absolutely dry, 1.5 dtex; cut length 6 mm.; Schwarzwälder Textil Werke)
1.5 kg. polyacrylonitrile (absolutely dry, 3.3 dtex, cut length 4 mm.; Schwarzwälder Textil Werke)
0.24 kg. Etadurin ® N 76 solution (Akzo Chemie, 12.5% weight Etadurin dry=3% by weight, referred to sulphite wood pulp).

c) Analogously to Example 1a), a fleece is produced from the following starting materials:
1000 liters water
3 kg. polyester (1.7 dtex, cut length 6 mm., absolutely dry; Schwarzwälder Textil Werke)
2 kg. linters (absolutely dry, Type 1471/941 of Peter Tenning GmbH)
0.48 kg. Etadurin ® N76 solution (12.5% by weight Etadurin N76, which corresponds to 0.06 kg. Etadurin dry=3% by weight, referred to linters).

EXAMPLE 2

Production of Carrier Materials Treated with Wet-Strength Agents by Impregnation of the Carrier Material with a Solution of a Wet-Strength Agent As starting material, there is used a carrier material of 60% polyester and 40% sulphite wood pulp (Type FW absolutely dry; Bayerische Zellstoff GmbH, density 0.3 g./cm³, liquid uptake 600 ml./m², weight per unit surface area 200 g./m², thickness 0.6 mm.). The carrier material is impregnated with an aqueous solution of 4 g./liter Etadurin ® N76, which corresponds to 3% by weight, referred to sulphite wood pulp, on an impregnation machine and subsequently dried at 100° C. to a residual moisture content of 3% by weight by means of circulating air.

EXAMPLE 3

Obtaining Further Starting Materials for the Production of Immune Reactive Porous Carrier Materials and for Carrying Out Tests A) Preparation of polyhapten, consisting of rabbit IgG and T3 or T4 bound thereon.

The preparation of polyhaptens is known from the prior art. Thus, for example, a digoxin-polyhapten can be obtained via reactive asymmetrical dicarboxylic acid ester-activated hapten ester and the binding thereof to a carrier protein.

The preparation of T3 and T4 polyhapten takes place, for example, by direct coupling of the $NH_2$ groups of hormone and protein by means of bis-imidates (see European Patent Specification No. 0,078,952) or by the carbodiimide reaction (see Aherne et al., Brit. J. Clin. Pharm., 3, 56/1976) or by the mixed anhydride reaction (see Erlanger et al., Methods in Immunology and Immunochemistry, ed. Williams and Chase, pub. Acad. Press, New York, 1967, p. 149 et seq.). Alternatively, the $NH_2$ functional group of T3 or T4 can be protected in a first step with acetyl, trifluoroacetyl, tert.-butoxycarbonyl or benzyloxycarbonyl groups. Subsequently, the carboxyl functional group is converted into an activated ester, for example an N-hydroxysuccinimide ester, N-hydroxyphthalimide ester of N-hydroxybenztriazole ester. An example of a so activated T4 is described in Example 3 of European Patent Specification No. 0,108,400. Reaction with the carrier protein, for example rabbit IgG, gives the polyhapten.

The choice of the carrier proteins is not subject to any limitations insofar as an appropriate "precipitating" antibody is available or can be produced.

B) Production of antibodies directed against the Fc part of the rabbit IgG.

Rabbit serum was subjected to an ammonium sulphate precipitation. After passage over DEAE-cellulose and papain cleavage according to the method of R. R. Porter (Biochem. J., 73, 119–126/1959), gel filtration over Sephadex G 100 and ion exchange chromatography over DEAE-cellulose according to the method described in the literature (see K. Malinowski and W. Manski in "Methods in Enzymology", J. J. Langone and H. van Vanukis eds., pub. Academic Press, Vol. 73, 418–459/1981), there are obtained the Fc fragments of the rabbit IgG as immunogens. Sheep are immunised with these immunogens and the appropriate antiserum obtained.

Antiserum directed against the Fc part of the rabbit IgG is purified via ammonium sulphate precipitation and passage over DEAE-cellulose to give the IgG fraction.

For the subsequent immunosorptive purification of antibodies, as carrier there is used the "affinity adsorber, glutardialdehyde activated" of Boehringer Mannheim GmbH (Order No. 665525). The immunosorption is carried out as described in the working instructions for the affinity adsorbent.

C) Obtaining of conjugate from antibody against T4 and β-D-galactosidase.

Antibody against T4 is coupled to β-D-galactosidase according to the instructions of T. Kitiwaga in Enzyme Immunoassay (eds. Ishikawa, Kawai and Migai, pub. Igaku Shoin, Tokyo/New York, 1981, pp. 81–89).

EXAMPLE 4

Production of Immune Reactive Porous Carrier Material (Homogeneous 1-Step Process)

200 mg. Polyhapten, consisting of rabbit IgG and T3 bound thereon, and 700 mg. antibody directed against the Fc part of the rabbit IgG (Heidelberger maximum) are taken up separately, in each case, in 1 liter of a solution of 0.05M acetic acid and 0.05% sodium chloride. After 30 minutes, the solutions are combined. The carrier material treated with wet-strength agent according to Example 1a) is impregnated with this solution and dried at 70° C. to a residual moisture content of 3% by weight.

EXAMPLE 5

Production of Immune Reactive Porous Carrier Material (Homogeneous 2-Step Process)

a) Carrier material which has been treated with wet-strength agent according to the instructions of Example 1a) is impregnated with a 0.5% by weight aqueous sodium chloride solution and dried at 70° C. to a residual moisture content of 3% by weight.

b) 200 mg. polyhapten, consisting of rabbit IgG and T4 bound thereon, and 700 mg. antibody directed against the Fc part of rabbit IgG (Heidelberger maximum) are each dissolved in 1 liter 0.05M acetic acid solution. After 30 minutes, the solutions are combined. The carrier material treated with wet-strength agent is impregnated with this solution and dried at 70° C. to a residual moisture content of 3% by weight.

EXAMPLE 6

Production of Immune Reactive Porous Carrier Material with Albumin 100 mg. Albumin and 350 mg. polyclonal antibody directed against albumin are separately taken up in 1 liter amounts of 0.05M acetic acid and 0.5% sodium chloride. After 30 minutes, the solutions are combined. The carrier material treated with wet-strength agent is impregnated with this solution and dried at 70° C. to a residual moisture content of 3% by weight.

EXAMPLE 7

Determination of the Matrix Binding M (Binding Strength)

Three types of carrier material are produced according to the procedure described in Example 1a). There are thereby used as wet-strength agents Etadurin® (Akzo Chemie)(fleece 1), Madurit® Type MW 150, Hoechst AG)(fleece 2) and Tylose® Type CBR 200 (Hoeschst AG)(fleece 3) in an amount of 3% by weight, referred to sulphite wood pulp. As comparison, there is thereby used a carrier material according to Example 1a) in the production of which, however, the use of wet-strength agent is omitted (fleece 4).

An immune reactive porous carrier material is produced from each of these carrier materials according to Example 4 by precipitation and drying.

The binding strength of the immune complexes on each of the immune reactive carriers is determined in an insert element according to FIG. 1 of the accompanying drawings with the use of a centrifugal analyser according to European Patent Specification No. 0,132,510. An insert element of similar construction is described in European Patent Specification No. 0,073,513.

For this purpose, from each of the four different immune reactive porous carrier materials there is cut out a matrix fleece (fleece 1–4) of the same size corresponding to the requirements of the insert element.

Provision of the insert elements according to FIG. 1

Chambers a, b, P, K, VK1, VK2, VK3: empty
Chamber c: 1 matrix fleece of the immune reactive porous carrier material
Chamber d: 1 substrate fleece (fleece impregnated with chlorophenol red-$\beta$-D-galactoside (CPR-G), 20 mMole/liter, HEPES 50 mMole/liter, pH 7.5).

Carrying out of the test 1. 50 $\mu$l. of a solution of 200 U/liter of conjugate of $\beta$-D-galactosidase as labelling and antibody against T4 in phosphate buffer (50 mMole/liter; pH 7.5) (with Crotein C® 0.5% and Tween® 20.3%) are pipetted into chamber c.

2. Incubation is carried out for 5 minutes. An immune complex is thereby formed from the immune complex X of polyhapten acting as antigen, consisting of rabbit IgG and T4 bound thereon, and antibody directed against the Fc part of the rabbit IgG with the conjugate of antibody against T4 acting as antibody and $\beta$-D-galactosidase as labelling.

3. Centrifuging is carried out for 20 seconds in a centrifugal analyser according to European Patent Specification No. 0,132,510, immune complexes Y, which are not firmly bound to the carrier, together with the solution, thereby being transported from chamber c into chamber d. All complexes Y which leave the chamber c because of poor binding to the matrix show $\beta$-galactosidase activity because of the incubation in step 2). The liquid thereby dissolves the reagents present in chamber d and takes them along into chamber VK3.

4. As soon as the centrifuging is finished, the solution leaves chamber VK3.

5. During the following renewed centrifuging, the solution flows into cuvette K. The $\beta$-galactosidase activity A (mE/min.) in the solution is there determined by absorption spectroscopic measurement at 576 nm of the change of the concentration of the product split from the substrate CPR-G. The measured enzyme activity is a measure of the amount of immune complex Y which, because of deficient binding strength, has been dissolved off from the immune reactive porous carrier. If there is no enzyme activity (A=O mE/min.), then the binding of the immune complex Y to the matrix is complete (blank value L=0%).

The enzyme activity is determined with this carrying out of the test for 4 insert elements, the chambers c of which are, in each case, provided with one of the matrix fleece 1, 2, 3 or 4.

Zero value

As zero value, there serves the result of the measurement of the enzyme activity A when, in the case of otherwise the same carrying out of the test, no immune reactive porous carrier material is placed in chamber c. Since, therefore, no immune complex Y can be formed and thus no binding to a matrix takes place, the zero value corresponds to a blank value L of 100%.

The zero value with a blank value of 100% can also be determined by placing in chamber c a carrier material treated with wet-strength agent which does not absorb the conjugate or only absorbs it to a very small extent.

The blank value L (%) of the fleece is calculated with the following equation:

$$L = \frac{E}{E_o} \times 100$$

The values obtained for the matrix fleece 1–4 are summarised in the following Table:

TABLE

| matrix fleece | wet-strength agent | enzyme activity A (mE/min.) | blank value L (%) |
| --- | --- | --- | --- |
| — | — | 2000 | 100 |
| 1 | Etadurin | 104 | 5.2 |
| 2 | Madurit | 36 | 1.8 |
| 3 | Tylose | 14 | 0.7 |
| 4 | — | 249 | 12.4 |

Thus, the blank value can be distinctly reduced by the use of the immune reactive porous carrier material according to the present invention.

It will be understood that the specification and examples are illustrative but not limitative of the present invention and that other embodiments within the spirit and scope of the invention will suggest themselves to those skilled in the art.

We claim:

1. Immune reactive porous carrier comprising a fiber containing porous carrier material having precipitated immune-complexes adsorbed thereon, wherein said fiber containing porous carrier has a density of from 0.2 to 0.5 g/cm$^3$ and has been pretreated with a wet strength agent prior to adsorption of said precipitate of said immune-complexes wherein said wet strength agent is selected from a group consisting of an epichlorohydrin resin, a melamine-formaldehyde resin, a urea-formaldehyde resin, a polyethyleneimine and carboxymethylcelluose.

2. Immune reactive porous carrier of claim 1, wherein said fibre containing material contains a mixture of cellulose and synthetic resin fibres.

3. Immune reactive porous carrier of claim 1, wherein said fibre containing material contains up to 95% by weight of synthetic resin fibres.

4. Immune reactive porous carrier of claim 1, wherein said fibre containing material contains up to 60% weight of synthetic resin fibres.

5. Immune reactive porous carrier of claim 1, wherein said fiber containing material comprises fibres of from 1 to 6 mm in length.

6. Immune reactive porous carrier of claim 1, containing from 0.05 to 6% by weight of wet strength agent.

7. Immune reactive porous carrier of claim 1, containing from 2 to 4% by weight of wet strength agent.

8. Immune reactive porous carrier of claim 1, wherein said precipitate of immune-complexes components which are present in a ratio equal to the Heidelberger maximum.

9. Immune reactive porous carrier of claim 1, wherein said precipitate of immune-complexes comprises polyhaptens and antibodies against said polyhaptens.

10. Immune reactive porous carrier of claim 9, wherein said polyhaptens comprises haptens and carrier proteins.

11. Immune reactive porous carrier of claim 10, wherein said antibodies are directed against carrier proteins.